(12) United States Patent
Bai et al.

(10) Patent No.: US 11,049,591 B2
(45) Date of Patent: Jun. 29, 2021

(54) SYSTEM FOR MONITORING AND ALERTING USERS OF DHA LEVELS

(71) Applicant: Société des Produits Nestlé S.A., Vevey (CH)

(72) Inventors: Manxi Bai, Beijing (CN); Jie Huang, Shanghai (CN)

(73) Assignee: Societe des Produits Nestle S.A., Vevey (CH)

(*) Notice: Subject to any disclaimer, the term of this patent is extended or adjusted under 35 U.S.C. 154(b) by 1062 days.

(21) Appl. No.: 14/989,861

(22) Filed: Jan. 7, 2016

(65) Prior Publication Data

US 2016/0196410 A1    Jul. 7, 2016

Related U.S. Application Data

(60) Provisional application No. 62/100,635, filed on Jan. 7, 2015.

(51) Int. Cl.
G16H 10/20 (2018.01)
G16H 20/60 (2018.01)
G16H 10/60 (2018.01)

(52) U.S. Cl.
CPC .............. G16H 10/20 (2018.01); G16H 10/60 (2018.01); G16H 20/60 (2018.01)

(58) Field of Classification Search
CPC .................................................. G06F 19/3475
See application file for complete search history.

(56) References Cited

U.S. PATENT DOCUMENTS

| 8,535,660 B1* | 9/2013 | Morrison | A61K 31/375 424/94.1 |
| 2007/0106129 A1 | 5/2007 | Srivathsa | |
| 2012/0009550 A1 | 1/2012 | Gayle | |
| 2013/0144919 A1* | 6/2013 | Firminger | G06F 16/13 707/803 |
| 2013/0216982 A1* | 8/2013 | Bennett | G09B 5/00 434/127 |

OTHER PUBLICATIONS

Kris-Etherton, Penny M., et al. "Dietary Reference Intakes for DHA and EPA." Prostaglandins, Leukotrienes and Essential Fatty Acids, vol. 81, No. 2-3, 2009, pp. 99-104., doi: 10.1016/j.plefa.2009.05.011. (Year: 2009).*

(Continued)

Primary Examiner — Gregory H Curran
(74) Attorney, Agent, or Firm — K&L Gates LLP

(57) ABSTRACT

A system and method is disclosed that establishes communication between a host system and a user device. The host system automatically registers individualized diet data received from the user device. The individualized diet data has parameters indicative of type and quantity of foods or supplements consumed by a user during a defined time period. The parameters are analyzed with a predetermined rule set indicative of concentrations of DHA in select foods and supplements to determine a level of the user's DHA dietary intake relative to a recommended intake. An alert is generated by the host system and transmitted via at least one predetermined communication method and without user intervention, responsive to the user's dietary intake relative to the recommended intake being a predetermined relation to a baseline.

14 Claims, 9 Drawing Sheets

(56) References Cited

OTHER PUBLICATIONS

XP021118529. Lisbeth, Dahl et al. "A Short Food Frequency Questionnaire to Assess Intake of Seafood and n-3 Supplements: Validation with Biomarkers." Nutrition Journal. vol. 10. No. 1. p. 127. Nov. 19, 2011.
XP021140971. Chien, Kuo-Liong et al. "A Taiwanese Food Frequency Questionnaire Correlates with Plasma Docosahexaenoic Acid but not with Plasma Eicosapentaenoic Acid Levels: Questionnaire and Plasma Biomarkers." BMC Medical Research Methodology, Biomed Central. vol. 13. No. 1. p. 23. Feb. 16, 2013.
International Search Report and Written Opinion dated Mar. 24, 2016 received in corresponding PCT Application No. PCT/IB2016/050066.

* cited by examiner

Informed consent of DHA intake assessment

DHA is extremely important for pregnant or lactating women, infant and people in other stages of their life 1. A customized food Frequency Questionnaire(FFQ) was administered to measure dietary intake of DHA by gathering information of your DHA containing diet in the last month 2. FFQ is a commonly used questionnaire, will not cause any harm to your body.

3. Your personal information and dietary conditions collected in this survey is only used for this assessment, will not be used for any other commercial purpose You can choose whether to agree to participate in this investigation

[ Agree ]  [ Disagree ]

Personal Data

| Name | | Age | |
| Height | | Weight | |
| Province | ▶ | City | ▶ |
| Email | |
| Education | ▶ |

Personal Data

| Name | test | Age | 23 |
| Height | 160 | Weight | 56 |
| Province | ▶ | City | ▶ |
| Email | 1661858097@qq.com |
| Education | ▶ |

[ Confirm ]

FIG. 5

| | | | | | | | | |
|---|---|---|---|---|---|---|---|---|
| Publish food | | | | | | | | |
| Food name | | | | | | | | |
| Food alias | | | | | | | | |
| Food ID | | | | | | | | |
| Food Picture | Select a file | | | | | | | |
| Size Picture | Select a file | # | | | | | | |
| Food category | Salty-Water seafood ○ | Fresh-Water seafood | Common food | Formula for mothers | Gels for mothers | | | |
| Total fatty acids (g/100 g of edible part) | | | | | | | | |
| DHA/total fatty acids (%) | | | | | | | | |
| DHA mg/100 g of edible part | | | | | | | | |
| Level of recommendation | | | | | | | | |

| DHA Management | | | | |
|---|---|---|---|---|
| | ID | Name Id | Age | Search by Name |
| 1282 | 342082 | | 26 | ***** ***** |
| 1281 | 342066 | | 28 | ***** ***** |
| 1280 | 342025 | | 28 | ***** ***** |
| 1279 | 342068 | | 33 | ***** ***** |
| 1278 | 442033 | | 33 | ***** ***** |

| All ▽ | Search by Doctor | | |
|---|---|---|---|
| Do *** | Date | Add on | |
| 9 | | | |
| 21 | | | |
| 34 | | | |
| 5 | | | |
| 6 | | | |

Participants Registration

| | | | |
|---|---|---|---|
| ID | 1220 | | |
| Name | **** | | |
| Age | 26 | | |
| Height | *** | | |
| Weight | 58 | | |
| Province | **** | | |
| City | **** | | |
| Email | | | |
| Education | | | |
| Food **** | | | |
| Food Name | Frequency | | |
| Crab | **** **** | 25 grams | |
| Lamb | **** **** | 125 grams | |
| **** **** | **** **** | | |
| **** **** | **** **** | | |
| **** **** | **** **** | | |
| **** **** | **** **** | | |
| | | Submit | |

SYSTEM FOR MONITORING AND ALERTING USERS OF DHA LEVELS

BACKGROUND

Docosahexaenoic acid (DHA), is an omega-3 long-chain polyunsaturated fatty acid (LCPUFA) that is not only a structural building block of cell membranes in the retina and brain, but also an essential nutrient for humans (Swanson, 2012).

It has been demonstrated in a large number of studies that a sufficient amount of DHA intake during pregnancy and lactation might not only help support brain and visual development of infants and toddlers, but also modulate immunity and improve sleeping (See for example, Mendez, 2009; Helland, 2003; Malcolm, 2003; Judge, 2007; Krauss-Etschmann, 2008; Cheruku, 2002; Furuhjelm C, 2009). Sufficient amount of DHA supplement is also beneficial to pregnant and lactating women. Some studies reported that DHA supplement during pregnancy may improve depressive symptoms of pregnant women and reduce the incidence of postpartum depression (Su, 2008; Freeman, 2006a; Avni-Barron, 2003). Additionally, Kulkarni et al. found that DHA supplements during pregnancy may reduce the risk of pre-eclampsia for pregnant women (Kulkarni, 2011). Freeman et al. demonstrated that the HAM-D score and EPDS score of patients with postpartum depression decreased 48.8% and 51.5% respectively after 8 weeks of DHA intervention (Freeman, 2006b).

On the other hand, it was also demonstrated in some studies that insufficient DHA intake during pregnancy or during a lactating period may not only have an impact on the health of pregnant women, but also on the development of infants and toddlers. Women's lack of DHA during pregnancy and lactating periods may also increase the risk of postpartum depression (Hibbeln, 2002). A survey with 8,998 Denmark pregnant women found that insufficient intake of fish during pregnancy (16-30 weeks) may increase the risk of premature and low-birth weight infants, and the incidence of intrauterine growth retardation (IUGR) was up to 6.6% (Olsen, 2002). Some studies demonstrated that pregnant and lactating women deficient of DHA may have direct impact on the intelligence of their offspring and may be associated with some diseases (Hibbeln, 2007; Lapillonne, 2010; McNamara, 2006).

Unfortunately, there are not many sources of DHA in foods that are available to pregnant and lactating women. Although humans may transform food and precursor fatty acid-α-linolenic acid (ALA) into DHA, the rate is very low (see for example, Swanson, 2012; Neff, 2011; Plourde, 2007; Harris, 2008). Therefore, a human needs to intake DHA from food. However, there are not many foods that contain DHA resulting in DHA deficiencies in humans. The main sources of food that contain DHA are algae and sea fish (Swanson, 2012).

Maternal DHA is the only source of DHA for a fetus, especially during the third trimester. The fetus, however, needs to acquire 67 mg DHA daily from their mother to fulfill their fast development requirements (Morse, 2012). Because women lose about 70-80 mg of DHA daily during the lactating period, a study has indicated that a maternal serum DHA level decreased 30% from 5 days to 6 weeks postpartum (Makrides, 2000). Therefore, additional DHA should be supplemented in pregnancy and lactation to fulfill the development of fetus, infants and toddlers.

In order to monitor the benefits of DHA and design dietary recommendations, it is important to evaluate DHA reference intake in the population. A food frequency questionnaire (FFQ) is a simple and feasible method. However, current FFQ has many items (Meng, 2008; Zhang, 2009), which are not focusing on DHA.

A study showed that about 90% of DHA intake for Chinese pregnant women originated from fish (Meng, 2008). Many studies have demonstrated that the dietary DHA intake of pregnant and lactating women may not only reflect DHA condition in the blood or breast milk, but also even DHA condition in the body of fetus, infants and toddlers (Meng, 2008; Zhang, 2009, Huang, 2013). Wakai et al. reported that the correlation coefficient between the amount of dietary fish and level of blood DHA is significant (Wakai, 2005).

The available clinical data on correlations between DHA intake and plasma/breast milk DHA level in pregnant and lactating women are summarized below:

Docosahexaenoic acid in maternal and neonatal plasma phospholipids and milk lipids (Huang, 2013) reported that the seafood intake of the mothers was positively and significantly related to the proportion DHA in breast milk ($r=0.35$, $p<0.05$). In this study, statistically significant and positive relationships were found for the proportions of DHA between breast milk and maternal plasma phospholipids. It is noteworthy that the observation that the fatty acid status of the infants with regard to DHA appeared to depend on the respective nutritional status of the mother ($r=0.46$, $p<0.01$)

Fish intake and serum fatty acid profiles from freshwater fish (Philibert, 2006) reported that fatty fish intake, particularly salmonid, and estimated EPA+DHA intake from fatty fish were significantly associated with serum EPA+DHA ($R2=0.41$ and 0.40, respectively).

Fish intake and estimated EPA, DPA and DHA in Japanese (Wakai, 2005) reported that the correlation between the amount of dietary fish and level of blood DHA is significant.

In summary, studies show that DHA is needed during pregnancy and periods of lactation. Although humans may transfer food and precursor fatty acid-α-linolenic acid (ALA) into DHA, the rate is very low, and varies from 0.013% to <0.01% (Swanson, 2012; Neff, 2011; Plourde, 2007; Harris, 2008). Therefore, humans need to intake DHA from food. But, there are not any systems that are known which receive information indicative of women's local diets, analyzes the information, and provides reports and recommendations to women and the healthcare providers to assist in maintaining proper DHA levels based upon their local diets. It is to such an improved system that the presently disclosed inventive concepts are directed.

SUMMARY

A method and system for monitoring and alerting users of DHA levels are disclosed. The problem of insufficient information with respect to maintaining proper DHA levels is addressed with computer systems configured to provide a tailored DHA intake Food Frequency Questionnaire (FFQ) based on regional foods in order to provide a simple and feasible evaluation method for DHA nutrition intervention. In the examples described herein, the FFQ is based upon regional diets in China. However, it should be understood that the FFQ could be based upon other regional diets. In some embodiments, the computer systems provide a short food self-evaluation scale based on validated FFQ and a Chinese food component list, which aims to identify the relationship between fish, algae and DHA level in blood and breast milk through DHA tests, thus validating the effect of a tailored FFQ on DHA intake and providing a simple and feasible tool to evaluate DHA intake.

BRIEF DESCRIPTION OF THE SEVERAL VIEWS OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, not every component may be labeled in every drawing.

FIG. 5 is an illustration of an exemplary user information input screen in accordance with some embodiments of the present disclosure.

FIG. 10 is an illustration of an exemplary food item form for separating and/or obtaining food items by a food item database of the host system in accordance with some embodiments of the present disclosure.

FIG. 11 is an illustration of an exemplary participant's information form for separating and/or obtaining participant's information by a user database of the host system in accordance with some embodiments of the present disclosure.

DETAILED DESCRIPTION

Figure 1:
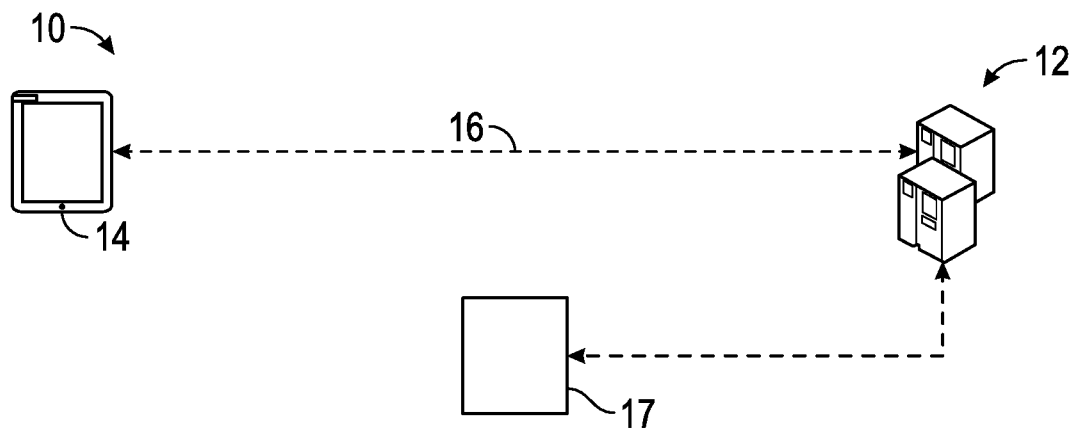
FIG. 1 is a diagrammatic view of hardware forming an exemplary embodiment of a system for monitoring and alerting users of DHA intake constructed in accordance with the present disclosure.

The methods and system proposed in this disclosure circumvent the problems described above. The present disclosure describes a system for monitoring and alerting users of DHA intake.

Before explaining at least one embodiment of the disclosure in detail, it is to be understood that the disclosure is not limited in its application to the details of construction, experiments, exemplary data, and/or the arrangement of the components set forth in the following description or illustrated in the drawings unless otherwise noted.

The systems and methods as described in the present disclosure are capable of other embodiments or of being practiced or carried out in various ways. Also, it is to be understood that the phraseology and terminology employed herein is for purposes of description, and should not be regarded as limiting.

The following detailed description refers to the accompanying drawings. The same reference numbers in different drawings may identify the same or similar elements.

As used in the description herein, the terms "comprises," "comprising," "includes," "including," "has," "having," or any other variations thereof, are intended to cover a non-exclusive inclusion. For example, unless otherwise noted, a process, method, article, or apparatus that comprises a list of elements is not necessarily limited to only those elements, but may also include other elements not expressly listed or inherent to such process, method, article, or apparatus.

Further, unless expressly stated to the contrary, "or" refers to an inclusive and not to an exclusive "or". For example, a condition A or B is satisfied by one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more, and the singular also includes the plural unless it is obvious that it is meant otherwise. Further, use of the term "plurality" is meant to convey "more than one" unless expressly stated to the contrary.

As used herein, any reference to "one embodiment," "an embodiment," "some embodiments," "one example," "for example," or "an example" means that a particular element, feature, structure or characteristic described in connection with the embodiment is included in at least one embodiment. The appearance of the phrase "in some embodiments" or "one example" in various places in the specification is not necessarily all referring to the same embodiment, for example.

Circuitry, as used herein, may be analog and/or digital components, or one or more suitably programmed processors (e.g., microprocessors) and associated hardware and software, or hardwired logic. Also, "components" may perform one or more functions. The term "component" may include hardware, such as a processor (e.g., microprocessor), a combination of hardware and software, and/or the like. Software may include one or more computer executable instructions that when executed by one or more components cause the component to perform a specified function. It should be understood that the algorithms described herein may be stored on one or more non-transient memory. Exemplary non-transient memory may include random access memory, read only memory, flash memory, and/or the like. Such non-transient memory may be electrically based, optically based, and/or the like.

In one example, a system and method is disclosed that establishes communication between a host system and a user device. The host system automatically registers individualized diet data received from the user device. The individualized diet data has parameters indicative of type and quantity of foods or supplements consumed by a user during a defined time period. The parameters are analyzed with a predetermined rule set indicative of concentrations of DHA in select foods and supplements to determine a level of the user's DHA dietary intake relative to a recommended intake. An alert is generated by the host system and transmitted via at least one predetermined communication method and without user intervention, responsive to the user's dietary intake relative to the recommended intake being a predetermined relation to a baseline. In this manner, the users are able to determine and monitor their DHA consumption and be automatically informed of recommendations to either increase or decrease the user's DHA consumption.

Referring now to the Figures, and in particular to FIG. 1, shown therein is a diagrammatic view of hardware forming an exemplary embodiment of a system 10 for monitoring and alerting users of DHA intake constructed in accordance with the present disclosure. The system 10 is provided with at least one host system 12, at least one user device 14, and a network 16. In some embodiments, the system 10 may include at least one external system 17 for use by doctors and/or other types of healthcare professionals (e.g., dietitians) to provide input with respect to evaluating and/or making recommendations with respect to a user's DHA intake. The system 10 may be a system or systems that are able to embody and/or execute the logic of the processes described herein. Logic embodied in the form of software instructions and/or firmware may be executed on any appropriate hardware. For example, logic embodied in the form of software instructions and/or firmware may be executed on dedicated system or systems, on a personal computer system, on a distributed processing computer system, and/or the like. In some embodiments, logic may be implemented in a stand-alone environment operating on a single computer system and/or logic may be implemented in a networked environment such as a distributed system using multiple computers and/or processors as depicted in FIG. 1, for example.

The host system 12 of the system 10 may include a single processor or multiple processors working together or independently to perform a task. In some embodiments, the host system 12 may be partially or completely network-based or cloud based. The host system 12 may or may not be located in single physical location. Additionally, multiple host systems 12 may or may not necessarily be located in a single physical location.

In some embodiments, the system 10 may be distributed, and include at least one host system 12 communicating with one or more user device 14 via the network 16. As used herein, the terms "network-based," "cloud-based," and any variations thereof, are intended to include the provision of configurable computational resources on demand via interfacing with a computer and/or computer network, with software and/or data at least partially located on a computer and/or computer network.

In some embodiments, the network 16 may be the Internet and/or other network. For example, if the network 16 is the Internet, a primary user interface of the system for monitoring and alerting users of DHA intake may be delivered through a series of web pages or private internal web pages of a company or corporation, which may be written in hypertext markup language. It should be noted that the primary user interface of the system 10 may be another type of interface including, but not limited to, a Windows-based application, a tablet based application, and/or the like.

The network 16 may be almost any type of network. For example, in some embodiments, the network 16 may be a version of an Internet network (e.g., exist in a TCP/IP-based network). It is conceivable that in the near future, embodiments within the present disclosure may use more advanced networking technologies.

In some embodiments, the one or more external systems 17 may optionally communicate with the host systems 12. For example, in one embodiment of the system 10, the one or more external systems 17 may supply data transmissions via the network 16 to the host system 12 regarding real-time or substantially real-time events (e.g., food source updates, photographic or illustration image updates, and/or individualized user recommendations). Data transmission may be through any type of communication including, but not limited to, speech, visuals, signals, textual, and/or the like. Events may include, for example, data transmissions regarding individualized user messages or updates from a physician, for example, initiated via the one or more external systems 17. It should be noted that the external systems 17 may be the same type and construction as the user device 14.

Figure 2:
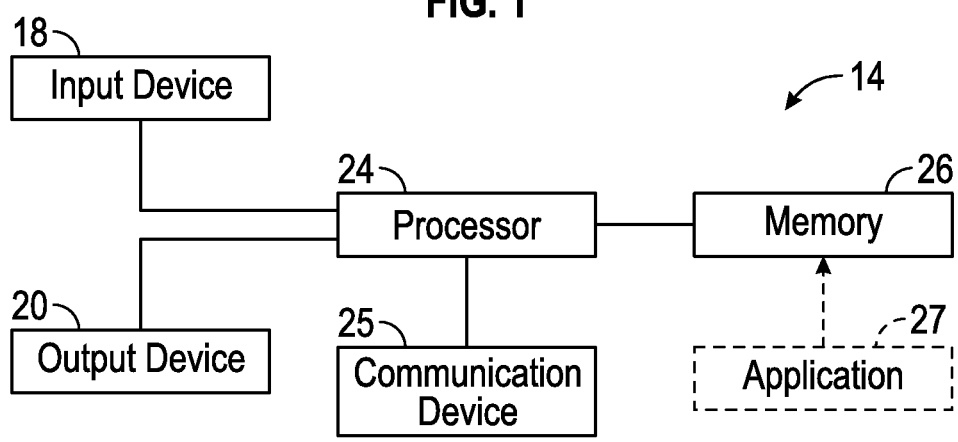
FIG. 2 is a diagrammatic view of an exemplary user device for use in the system for monitoring and alerting users of DHA intake illustrated in FIG. 1.

As shown in FIG. 2, the one or more user devices 14 of the system 10 may include, but are not limited to implementation as a personal computer, a cellular telephone, a smart phone, a network-capable television set, a tablet, a laptop computer, a desktop computer, a network-capable handheld device, a server, a digital video recorder, a wearable network-capable device, and/or the like.

In some embodiments, the user device 14 may include one or more input devices 18, one or more output devices 20, one or more processors 24, one or more communication device 25 capable of interfacing with the network 16, one or more non-transient memory 26 comprising processor executable code and/or software application(s), for example including, a web browser capable of accessing a website and/or communicating information and/or data over a wireless or wired network (e.g., network 16), and/or the like. The one or more non-transient memory 26 may also store a DHA intake application 27 that, when executed by the one or more processors 24 causes the user device 14 to collect information with respect to the user's diet that can be used to determine the user's DHA intake. In some embodiments, the DHA intake application 27 causes the one or more processors 24 to provide a FFQ tailored to determine DHA intake to the one or more output devices 20, and to receive information from the user via the one or more input devices 18. Such information can be stored either temporarily and/or permanently in the one or more non-transient memory 26 and/or transmitted to the host system 12 via the network 16 and the communication device 25.

Embodiments of the system 10 for monitoring and alerting users of DHA intake may also be modified to use any user device 14 or future developed devices capable of communicating with the host system 12 via the network 16.

The one or more input devices 18 may be capable of receiving information input from a user and/or processor(s), and transmitting such information to other components of the user device 14 and/or the network 16. The one or more input devices 18 may include, but are not limited to, implementation as a keyboard, touchscreen, mouse, trackball, microphone, fingerprint reader, infrared port, slide-out keyboard, flip-out keyboard, cell phone, PDA, remote control, fax machine, wearable communication device, network interface, combinations thereof, and/or the like, for example.

The one or more output devices 20 may be capable of outputting information in a form perceivable by a user and/or processor(s). For example, the output devices 20 may include, but are not limited to, implementations as a computer monitor, a screen, a touchscreen, a speaker, a website, a television set, a smart phone, a PDA, a cell phone, a fax machine, a printer, a laptop computer, combinations thereof, and the like, for example. It is to be understood that in some exemplary embodiments, the input device 18 and the output device 20 may be implemented as a single device, such as, for example, a touchscreen or a tablet. It is to be further understood that as used herein the term user is not limited to a human being, and may comprise, a computer, a server, a website, a processor, a network interface, a human, a user terminal, a virtual computer, combinations thereof, and/or the like, for example.

The one or more host systems 12 may be capable of interfacing and/or communicating with the user devices 14 and the external systems 17 via the network 16. For example, the host systems 12 may be configured to interface by exchanging signals (e.g., analog, digital, optical, and/or the like) via one or more ports (e.g., physical ports or virtual ports) using a network protocol, for example. Additionally, each host system 12 may be configured to interface and/or communicate with other host systems directly and/or via the network 16, such as by exchanging signals (e.g., analog, digital, optical, and/or the like) via one or more ports.

The network 16 may permit bi-directional communication of information and/or data between the host system 12, the user devices 14, and/or the external systems 17. The network 16 may interface with the host system 12, the user devices 14 and/or the external systems 17 in a variety of ways. For example, in some embodiments, the network 16 may interface by optical and/or electronic interfaces, and/or may use a plurality of network topographies and/or protocols including, but not limited to, Ethernet, TCP/IP, circuit switched path, combinations thereof, and/or the like. For example, in some embodiments, the network 16 may be implemented as the World Wide Web (or Internet), a local area network (LAN), a wide area network (WAN), a metropolitan network, a 4G network, a satellite network, a radio network, an optical network, a cable network, a public switch telephone network, an Ethernet network, combinations thereof, and the like, for example. Additionally, the network 16 may use a variety of network protocols to permit bi-directional interface and/or communication of data and/or information between the host system 12, the user devices 14 and/or the external systems 17.

Figure 3:
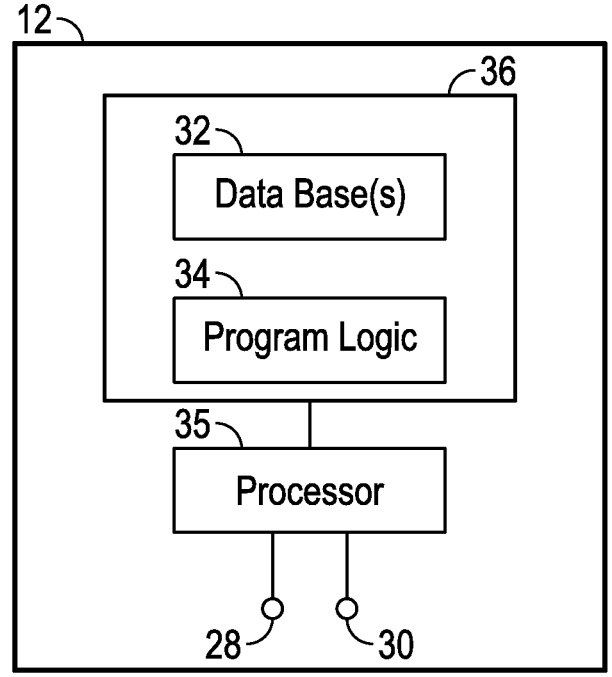
FIG. 3 is a diagrammatic view of an exemplary embodiment of a host system for use in the system for monitoring and alerting users of DHA intake illustrated in FIG. 1.

Referring now to FIG. 3, shown therein is a diagrammatic view of an exemplary embodiment of the host system 12. In the illustrated embodiment, the host system 12 is provided with a database 32, program logic 34, and one or more processor 35. The program logic 34 and the database 32 are stored on non-transitory computer readable storage media 36 accessible by the processor 35 of the host system 12. It should be noted that as used herein program logic 34 is another term for instructions which can be executed by the processor 24 or the processor 35. The database 32 can be a relational database. Examples of such databases comprise, DB2®, Microsoft® Access, Microsoft® SQL Server, Oracle®, mySQL, PostgreSQL, and the like. The database 32 can be centralized or distributed across multiple systems.

In some embodiments, the host system 12 may comprise one or more processors 35 working together, or independently to, execute processor executable code stored on the one or more non-transitory storage media. Additionally, each host system 12 may include at least one input device 28 and at least one output device 30. Each element of the host system 12 may be partially or completely network-based or cloud-based, and may or may not be located in a single physical location.

The processor 35 may be implemented as a single processor or multiple processors working together, or independently, to execute the program logic 34 as described herein. It is to be understood, that in certain embodiments using more than one processor 35, the processors 35 may be located remotely from one another, located in the same location, or comprising a unitary multi-core processor. The processors 35 may be capable of reading and/or executing processor executable code and/or capable of creating, manipulating, retrieving, altering, and/or storing data structures into the one or more non-transitory storage media 36.

Exemplary embodiments of the processor 35 may be include, but are not limited to, a digital signal processor (DSP), a central processing unit (CPU), a field programmable gate array (FPGA), a microprocessor, a multi-core processor, combinations, thereof, and/or the like, for example. The processor 35 may be capable of communicating with the one or more non-transitory storage media 36 via a path (e.g., data bus). The processor 35 may be capable of communicating with the input devices 28 and/or the output devices 30.

The processor 35 may be further capable of interfacing and/or communicating with the user devices 14 and/or the external systems 17 via the network 16. For example, the processor 35 may be capable of communicating via the network 16 by exchanging signals (e.g., analog, digital, optical, and/or the like) via one or more ports (e.g., physical or virtual ports) using a network protocol to provide the FFQ (or updated FFQ) to the one or more user devices 14, receive information from the one or more user devices 14 indicative of the users' diets that can be correlated to their DHA intake.

The one or more non-transitory storage media 36 may be capable of storing processor executable code. Additionally, the one or more non-transitory storage media 36 may be implemented as a conventional non-transient memory, such as for example, random access memory (RAM), CD-ROM, a hard drive, a solid state drive, a flash drive, a memory card, a DVD-ROM, a disk, an optical drive, combinations thereof, and/or the like, for example.

In some embodiments, the one or more non-transitory storage media 36 may be located in the same physical location as the host system 12, and/or one or more non-transitory storage media 36 may be located remotely from the host system 12. For example, the one or more non-transitory storage media 36 may be located remotely from the host system 12 and communicate with the processor 35 via the network 16. Additionally, when more than one non-transitory storage media 36 is used, a first non-transitory storage media 36 may be located in the same physical location as the processor 35, and additional non-transitory storage media 36 may be located in a remote physical location from the processor 35. Additionally, one or more non-transitory storage media 36 may be implemented as a "cloud" non-transitory storage media (i.e., one or more non-transitory storage media 36 may be partially or completely based on or accessed using the network 16).

The one or more input devices 28 of the host system 12 may transmit data to the processor 35 and may be similar to the input device 18 of the user device 14. The input devices 28 may be located in the same physical location as the processor 35, or located remotely and/or partially or completely network-based. The one or more output devices 30 of the host system 12 may transmit information from the processor 35 to a user, and may be similar to the output device 20 of the user device 14. The output devices 30 may be located with the processor 24, or located remotely and/or partially or completely network-based.

The one or more non-transitory storage media 36 may store processor executable code and/or information comprising one or more databases 32 and program logic 34. In some embodiments, the processor executable code may be stored as a data structure, such as the database 32 and/or data table, for example.

As illustrated in FIGS. 4-8, the system 10 for monitoring and alerting users of DHA intake may include the DHA intake application 27 executed by the processor 24 of the user device 14 that is capable of communicating with the host system 12 via the network 16. The system 10 may include a separate program, application or "app", or a widget, each of which may correspond to instructions stored in a non-transient, tangible storage medium for execution by a processor 24 of the user device 14. Alternately, the system 10 may include instructions stored in a non-transient, tangible storage media for execution by the processor 35 of the host system 12 with results sent via the network 16 to be displayed on the output device 20 of the user device 14.

The instructions of the DHA intake application 27, when executed by the processor 24 of the user device 14, cause the user device 14 to perform certain tasks. For example, such tasks may include displaying content such as a login screen 40, a home screen 46, an information input screen 52, a food item selection screen 60, a frequency and portion size selection screen 70, and an output screen 80. As illustrated in FIGS. 4-8, the login screen 40, the home screen 46, the information input screen 52, the food item selection screen 60, the frequency and portion size selection screen 70, and the output screen 80 are shown as such screens may appear on the output device 20 of the user device 14, such as an Apple® iPhone® or iPad®. The DHA intake application 27 may be implemented for use on other types of user devices 14 including, but not limited to, other mobile devices, personal computers, or laptop computers, with appropriate storage and processing capacity and internet or network connectivity. A user of the system 10 may interact via user interface implementations of the user device 14 such as, for instance, by using the touchscreen of the Apple® iPhone® or iPad®. In some embodiments of the system 10, certain viewable screens of the DHA intake application 27 may be designed to switch from portrait to landscape presentation of the output device 20 of the user device 14 depending on the current orientation of the user device 14 being utilized. Such functionality is optional, and has no adverse impact on the functionality of the DHA intake application 27.

It should also be noted that where necessary, desirable, or both, the food and supplement intake questions of the system 10 may be administered manually, for instance, by a physician and then entered into the system 10 via the input device 28 of the host system 12.

Figure 4:
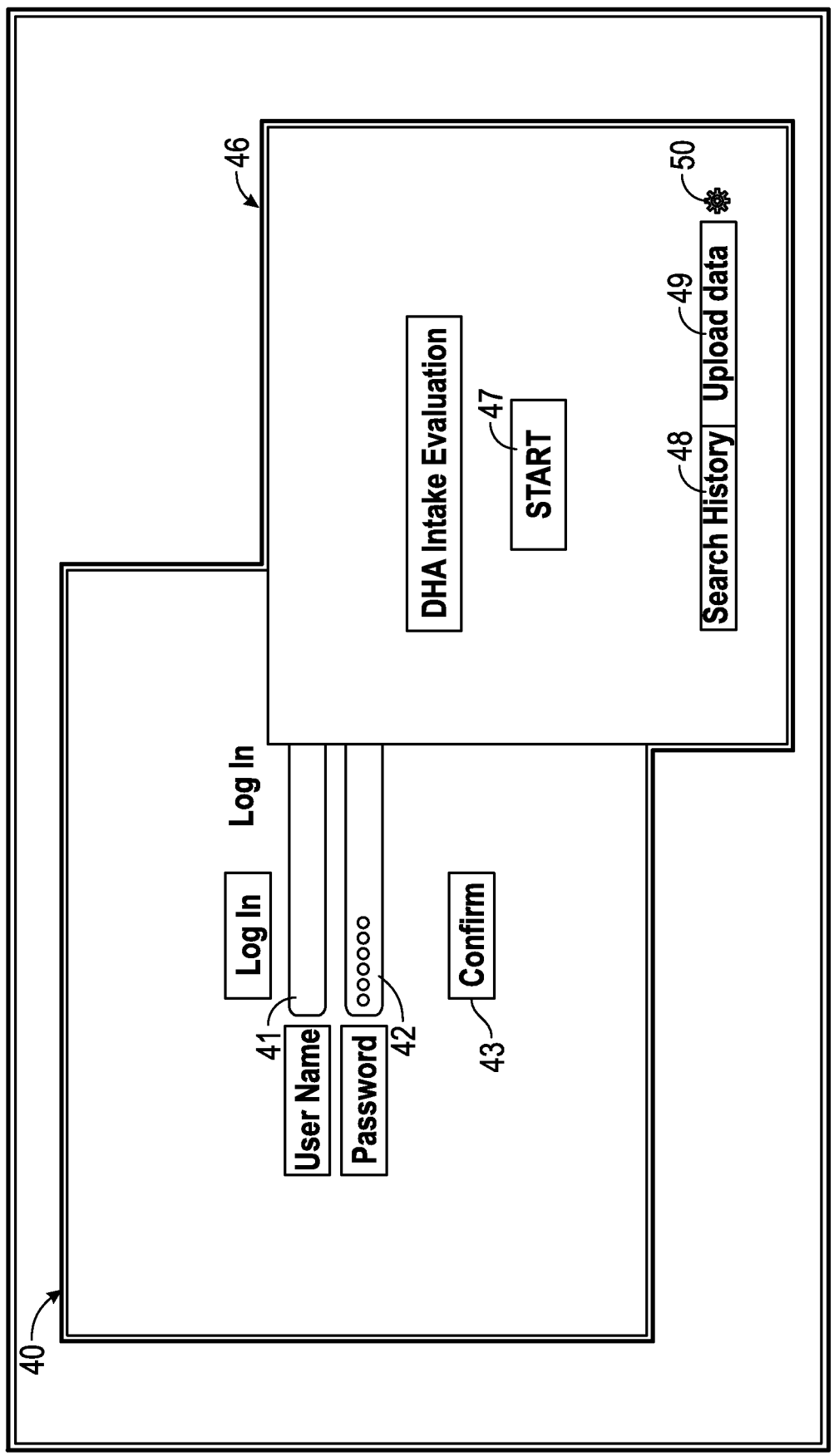
FIG. 4 is an illustration of an exemplary login and start screen in accordance with some embodiments of the present disclosure.

Referring now to FIG. 4, an exemplary login screen 40 of the DHA intake application 27 is shown. The login screen 40 of the DHA intake application 27 may have regions designed for input from the user associated with, for instance, a user ID 41, and a password 42. In some embodiments of the system 10, the login screen 40 of the DHA intake application 27 may also include a password retrieval function (not shown) in the event a user loses or cannot remember their password to access the host system 12. An alternative login function (not shown) may also be present on the login screen 40, which provides login functionality and allows a user to login to the system 10 via other authentication or verification methods such as through the social networks Linkedin.com, or Facebook.com. Some embodiments of the system 10 may also allow a new user to register their information from the login screen 40 of the DHA intake application 27.

Also shown in FIG. 4 is an exemplary home screen 46 of the DHA intake application 27. By using a start button 47 or other suitably assigned or programmed button or interactivity option (such as swiping) available on the user device 14, a user may begin a DHA intake FFQ. In addition, the home screen 46 may include menu items such as a search history region 48, an upload data region 49, a settings region 50, and/or an alerts region (not shown). Each of these respective regions allows a user to access the various aspects of the DHA intake application 27. The menu regions offer navigational function in the DHA intake application 27, however, it will be understood by one skilled in the art that such functionality is optional, and has no adverse impact on the functionality of the DHA intake application 27.

FIG. 5 illustrates an exemplary information input screen 52 of the DHA intake application 27. The information input screen 52 provides input regions 54 designed to accept input from a user. The information input screen 52 input regions 54 may be associated with appropriate fields in the database 32 accessible by the host system 12 of the system 10. Once information (e.g., name, age, height, weight, providence, city, email address, and education) has been put into the input regions 54, users may transmit the information via the network 16 from communication device 25 of the user device 14 to the host system 12 for registration in the database 32, by selecting, for instance, a save button (not shown) or other appropriately programmed button or other mechanism. As illustrated, the DHA intake application 27 may include a confirmation screen 56. The confirmation screen 56 may, for instance, allow a user to verify they have entered the correct information in the input regions 54 before the information is transmitted via the network 16 from the communication device 25 of the user device 14 to the host system 12 for registration in the database 32. However, if there is no connection via the network 16, the data may be temporarily stored internally in the memory 26 of the user device 14 until a connection to the network 16 can be established. In another embodiment of the system 10, the DHA intake application 27 may transmit the information to the host system 12 dynamically in real time as it is entered by the user. In still another embodiment of the system 10, the DHA intake application 27 may transmit the information to the host system 12 at predetermined intervals.

Also illustrated in FIG. 5, the DHA intake application 27 may include an informed consent region 57. The informed consent region 57 displayed on the information input screen 52 of the DHA intake application 27 may be included, for instance, where required by law, or when the user elects to share their information with third party(ies), for instance their physician. The informed consent region 57 may include an agree region 58 whereby the user may signal their consent to the terms contained in the informed consent region 57 by selecting the agree region 58. The informed consent region may also include a disagree region 59 whereby the user may signal that they do not agree with the terms contained in the informed consent region 57 by selecting the disagree region 59. It will be understood by one skilled in the art that the informed consent region 57 is optional and has no adverse impact on the DHA intake application 27.

Figure 6:
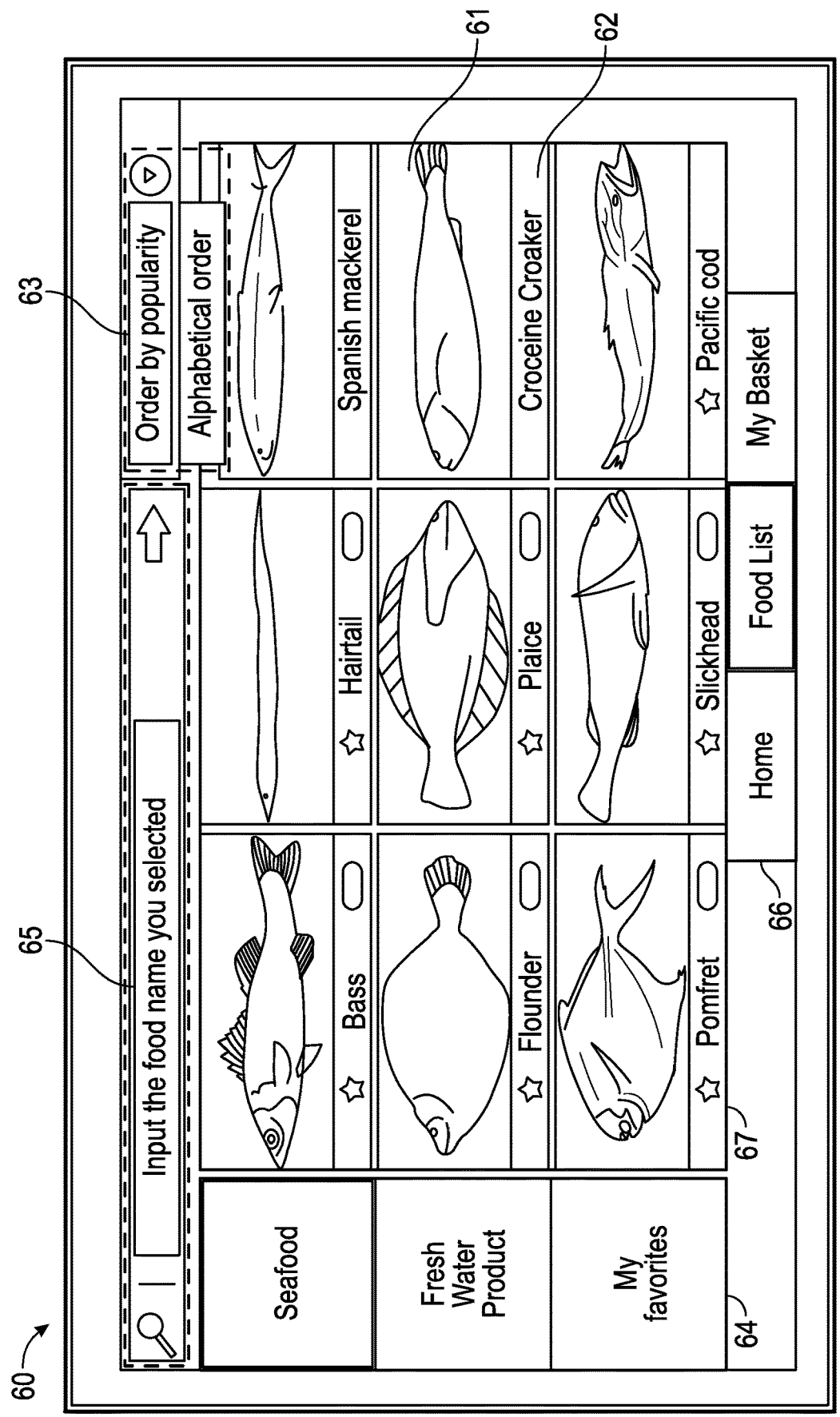
FIG. 6 is an illustration of an exemplary food item selection screen in accordance with some embodiments of the present disclosure.

FIG. 6 illustrates an exemplary food item selection screen 60 of the DHA intake application 27. The food item selection screen 60 is designed to allow the user to indicate the food item(s) consumed by selecting items from the food item selection region 67, for instance, a text description 62, a photographic image 61, or an illustrated image (not shown). The user may customize how the food item selection region 67 is displayed on the output device 20 of the user device 14 by changing, for instance, the order in which the items are displayed using the item order region 63, or the types of products displayed using the item type region 64. The user may also narrow the search list of items by inputting the desired parameters and executing a search using a search region 65. It will be understood by one skilled in the art that customization of the food item selection region 67 is optional functionality, and has no adverse impact on the functionality of the DHA intake application 27. In addition to food items, the food item selection region 67 may also include supplements displayed and selected in a similar fashion to the food items described above. In one embodiment of the system 10 the DHA intake application 27 may transmit the food items selected in real time, without user intervention, from the communication device 25 of the user device 14 via the network 16 to the host system 12 where the selected food items are registered in the database 32. In another embodiment, the selected food items may be transmitted when the user selects, for instance, submit, next, save, or other appropriately programmed option, indicating that the DHA intake application 27 should transmit the information. In another embodiment, the DHA intake application 27 may transmit the information at predetermined intervals.

Figure 7:
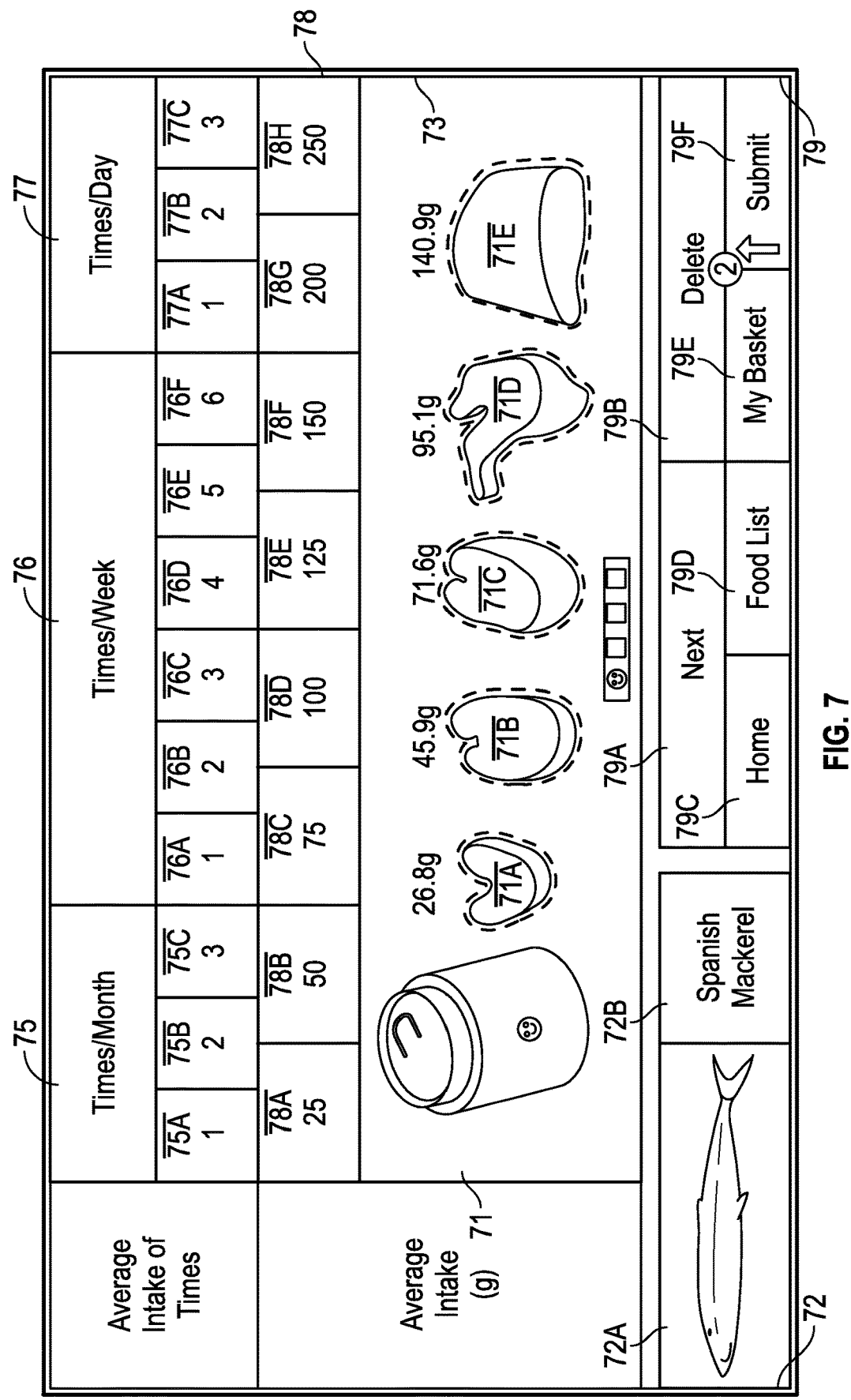
FIG. 7 is an illustration of an exemplary frequency and portion size selection screen in accordance with some embodiments of the present disclosure.

FIG. 7 illustrates an exemplary frequency and portion size selection screen 70 of the DHA intake application 27 of the system 10. The frequency and portion size selection screen 70 includes an intake portion region 73, an intake frequency region 74, an item selection region 72, and a frequency and portion navigation region 79

The intake frequency region 74 may include a month region 75, a week region 76, and a day region 77. The month region 75, may also include monthly frequency regions 75A-C, the week region 76 may also include weekly frequency regions 76A-F, and the day region 77 may include daily frequency regions 77A-C, all designed to allow a user to select the frequency of intake of a selected food during a defined time period. In one embodiment of the DHA intake application 27, selection of at least one of the monthly frequency regions 75A-C, the weekly frequency regions 76A-F, and the daily frequency regions 77A-C, causes the program logic of the DHA intake application 27 to perform an action, such as, for instance, transmitting the selected information from the communication device 25 of the user device 14 via the network 16 to the host system 12 for registration in the database 32. In another embodiment of the DHA intake application 27, selection of at least one of the monthly frequency regions 75A-C, the weekly frequency regions 76A-F, and the daily frequency regions 77A-C, causes the program logic of the DHA intake application 27 to perform an action, such as, for instance, storing the information in the memory 26 of the user device 14.

The intake portion region 73 may include a numerical region 78 and a scaled image region 71. The numerical region 78 may include numerical portion regions 78A-H, and the scaled image region 71 may include portion image regions 71A-E, all of which, when selected, cause the program logic of the DHA intake application 27 to perform an action. Those actions may be, but are not limited to, storing the selections in the memory 26 of the user device 14, and transmitting via the communication device 25 of the user device 14 over the network 16 to the host system 12 the selections to be registered in the database 32. It will be understood by one of ordinary skill in the art that selections may be stored temporarily in the memory 26 of the user device 14 for transmission at a later time, either predetermined, or upon user selection.

The selected item region 72 may include at least one of an item image region 72A and an item description region 72B.

The frequency and portion navigation region 79 may include, for instance a next region 79A, a back region (not shown), a delete region 79B, a home region 79C, a food list region 79D, a my basket region 79E, and a submit region 79F. Regions 79A-F allow a user to navigate the frequency and portion size selection screen 70 and/or the DHA intake application 27. For instance, the next region 79A may be included to allow a user to move to the next food item or supplement from their selected list to select the portion size and frequency for that food item or supplement. The selection of desired regions of the frequency and portion size selection screen 70 may be done using a touchscreen, a mouse, or any other suitable means compatible with the user device 14.

The selected foods and/or supplements, the portion size, and the frequency of intake, when associated with a user, are parameters that represent individualized diet data. In one embodiment of the system 10, parameters of the individualized diet data selected in the food item selection screen 60 and the frequency and portion size selection screen 70 of the DHA intake application 27 may be transmitted by the communication device 25 of the user device 14 via the network 16 to the host system 12 and registered in the database 32. The parameters of the individualized diet data registered in the database 32 are analyzed utilizing the program logic 34 by the processor 35 of the host system 12, in real time, without user intervention, using rule sets in the database 32 containing DHA concentrations in select foods, supplements, or a combination of both. The rule sets can be predetermined and/or the methods and systems can employ Artificial Intelligence techniques such as machine learning and iterative learning to generate the rule sets. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g., Expert inference rules generated through a neural network or production rules from statistical learning).

Using the analyzed parameters, the host system 12 of the system 10 generates an individualized DHA dietary intake indicative of the users DHA intake for the defined time period. The program logic 34 causes the individualized DHA dietary intake to be compared by the processor 35 of the host system 12 in real time, without user intervention, to relative recommended intake levels in the database 32 associated with a category of persons. The categories of persons may include pregnant women, and lactating women. It should be noted that the categories of persons may be further defined such as by trimester, or month of pregnancy, or by month or quarter for lactating or postpartum women, with different recommended intake levels associated with each in the database 32. The host system 12 then automatically generates at least one of a report and an alert that may be sent to a target audience (e.g. the user and/or party(ies)) via at least one predetermined communication method from the output device 30 of the host system 12 via the network 16. The at least one predetermined communication method (s) may include, but is not limited to, email, text message, facsimile, and on-screen display on the output device 20 of the user device 14 (see FIG. 8) or the external system 17. The at least one of a report and an alert may also be sent to a third party, or third parties, as selected by the user, for instance, on the information input screen 52 of the DHA intake application 27 and registered in the database 32 of the host system 12. The third party(ies) may be, but are not limited to, physicians, midwifes, doulas, caretakers, hospitals, clinics, or other healthcare professionals. In one embodiment of the system 10, the at least one of a report and alert may be transmitted from the output device 30 of the host system 12 to third party(ies) automatically, without user intervention. In another embodiment, the at least one of a report and alert may be transmitted from the output device 30 of the host system 12 to third party(ies) when selected by the user on a case by case basis, meaning, the user may select to send one or more reports by selecting, for instance, a send to region (not shown) of the output screen 80 in the DHA intake application 27, or other appropriately programmed option. The at least one of a report and alert may include, but are not limited to, individualized DHA intake, a recommended DHA intake, dietary recommendations, DHA level warnings, personalized messages, general recommendations from a physician, personalized messages from a physician, follow up instructions, other pertinent information, or a combination of two or more of the preceding.

Figure 8:
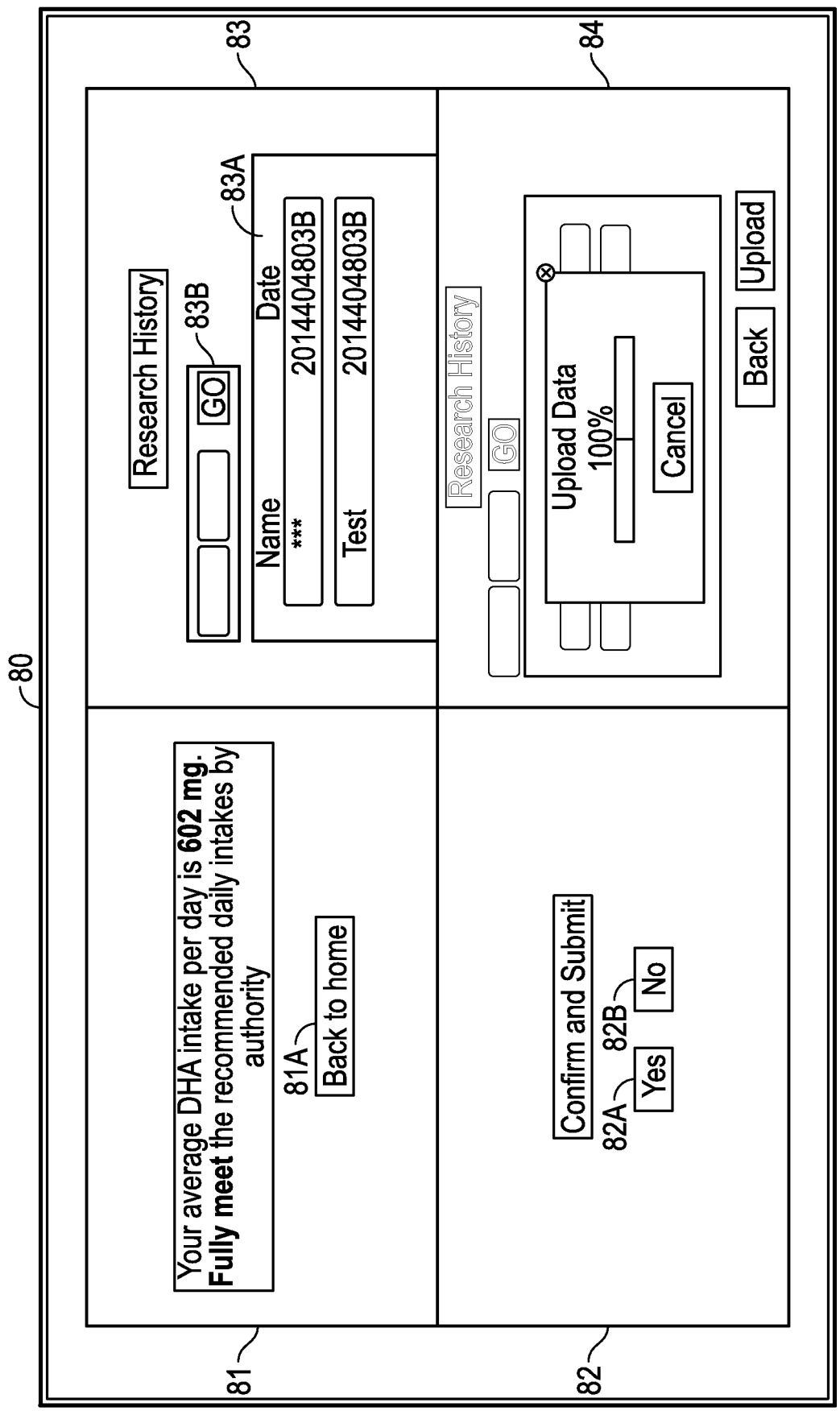
FIG. 8 is an illustration of an exemplary output screen in accordance with some embodiments of the present disclosure.

FIG. 8 illustrates an exemplary output screen 80 of the DHA intake application 27. The output screen 80 is provided with an alert region 81, a confirm and submit region 82, a history region 83, and optionally, an upload screen 84. The alert region 81 may include a navigation button such as, for instance, back to home region 81A or close report (not shown). The confirm and submit region 82 may include a yes region 82A and a no region 82B, or similar regions designed to allow the user to accept or reject the information in the confirm and submit region 82 of the DHA intake application 27 displayed on the output device 20 of the user device 14. The history region 83 may include a history display region 83A and a history search region 83B. The output screen 80 of the DHA intake application 27 may optionally include an upload screen 84.

Figure 9:
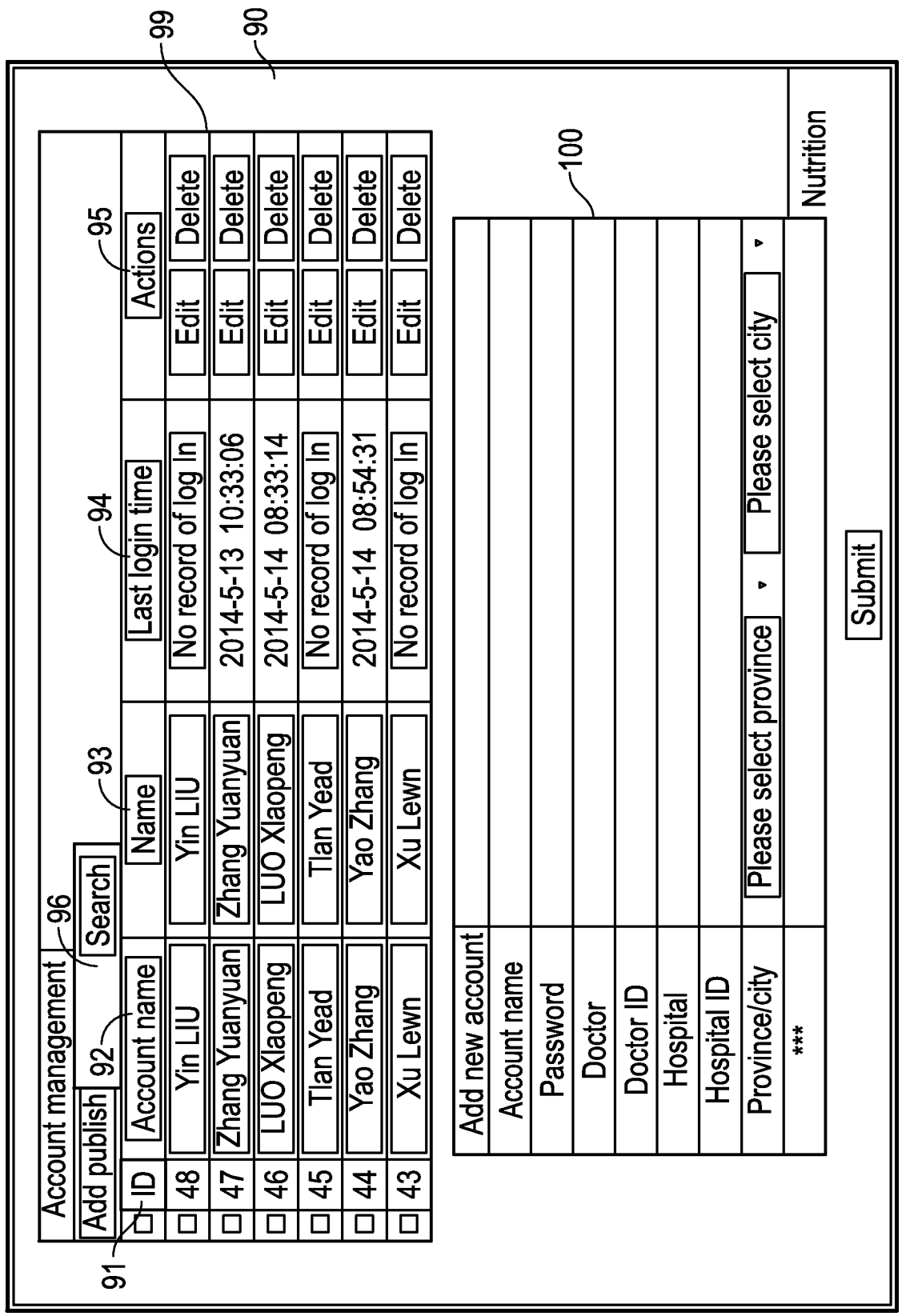
FIG. 9 is an illustration of an exemplary user information form for separating and/or obtaining user information by a user database of the host system in accordance with some embodiments of the present disclosure.

FIG. 9 illustrates an exemplary user information form 90 for separating and/or obtaining user information by a user database 32 of the host system 12 in accordance with one embodiment of the system 10. The user information form 90 is provided with an account management region 99 and an account add/edit region 100. The account management region 99 may include, for instance, a user ID region 91, an account name region 92, a user name region 93, a login history region 94, an actions regions 95, and an user search region 96.

The account add/edit region 100 is provided with regions designed for input by a user. The input regions of the account add/edit region 100 may include, but are not limited to, add new account, account name, password, doctor, doctor ID, hospital, hospital ID, province/city, please select province, please select city, and submit. The regions in the account add/edit region 100 may be associated with appropriate fields in the database 32. In one embodiment of the system 10, a user may input information in the regions of the account add/edit region 100 using the input device 28 of the host system 12. When submitted, the program logic 34 of the system 10 causes the host system 12 to register the completed regions of the account edit/add region 100 of the user information form 90 in the database 32.

FIG. 10 illustrates an exemplary food item form 110 for separating and/or obtaining food item information by a user database 32 of the host system 12 in accordance with one embodiment of the system 10. The food item form 110 is provided with regions designed to accept input from a user. The regions of the food item form may include, but are not limited to, publish food, food name, food alias, food ID, food picture, size picture, food category, total fatty acids (g0100 g of edible part), DHA/total fatty acids (%), DHA mg/100 g of edible part, level of recommendation, salty-water seafood, fresh-water seafood, common food, formula for mothers, food item region (not shown), frozen (not shown), fresh (not shown), dried (not shown), canned (not shown), pickled (not shown), freeze-dried (not shown), and gels for mothers. The regions of the food item form 110 are associated with appropriate fields in the database 32. The food item form 110 may be designed to allow a user to add new food items or supplements to the database 32. In one embodiment of the system 10, a user may input information into the regions of the food item form 110 using the input device 28 of the host system 12, when submitted, the program logic 34 of the system 10 causes the host system 12 to register the completed regions of the food item form 110 in the database 32 in such new food items may be included in an updated FFQ, tailored for DHA intake, which is transmitted to the user devices 14.

FIG. 11 illustrates an exemplary participant information form 120 for separating and/or obtaining participant information by the database 32 of the host system 12 in accordance with one embodiment of the system 10. The participant information form 120 is provided with a participant management region 122 and a participant add/edit region 124. The participant management region 122 may include, for instance, a participant ID region, a participant name ID region, an assessment address region, a doctor number region, a doctor region, a date region, an actions region, a date search region, and a doctor search region.

The participant add/edit region 124 is provided with regions designed for input by a user. The input regions of the participant add/edit region 124 may include, but are not limited to, a participant information region 126, a food intake region 127, a doctor information region 128, an assessment results region 129, and an assessment date region 130.

The participant information region 126, food intake region 127, doctor information region 128, assessment results region 129, and assessment date region 130 in the participant add/edit region 124 may be associated with appropriate fields in the database 32 of the system 10. In one embodiment of the system 10, a user may input information in the regions of the participant add/edit region 124 using the input device 28 of the host system 12, when submitted, the program logic 34 of the system 10 causes the host system 12 to register the completed regions of the participant add/edit region 124 of the participant information form 120 in the database 32.

The participant information region 126 of the participant add/edit region 124 may include regions designed to accept input from a user. Exemplary regions include, but are not limited to, an ID region, a name region, an age region, a height region, a weight region, a province region, a city region, an email region, a phone number region (not shown), an address region (not shown), and an education region. The regions of the participant information region 126 of the participant add/edit region 124 may be associated with appropriate fields in the database 32 of the system 10. The regions of the participant information region 126 may be used to separate and/or obtain personally identifiable information about a participant that may be used, for instance, to uniquely identify the participant, categorize the participant in a study, or associate the participant with a relevant region or locale. In addition, information entered in some regions of the participant information region 126, for instance, the email region, the phone number region (not shown), or the address region (not shown) may be used by the host system 12 of the system 10 to send at least one of a report and alert from the output device 30 in response to certain events. These events may include, but are not limited to, completion of an DHA intake FFQ, a DHA dietary intake relative to a recommended intake, a DHA dietary intake being below a predefined level relative to a recommended intake, a current DHA dietary intake being different from a past DHA dietary intake, sending a dietary recommendation responsive to the DHA dietary intake relative to the recommended intake being a predetermined relation (e.g., above or below) a predefined baseline, and an updated DHA dietary intake relative to the recommended intake being a predetermined relation (e.g., above or below) a predefined baseline.

The food intake region 127 of the participant add/edit region 124 may include regions designed to accept input from a user. Exemplary regions include, but are not limited to, a food items region, a frequency region, and an intake amount of each item region. The regions of the food intake region 127 may be associated with appropriate fields in the database 32 of the system 10. It will be recognized by one skilled in the art that the regions of the food intake region 127 are associated with the food and/or supplement items, the portion size, and the frequency of intake, which may be selected by a participant completing the DHA intake FFQ. When, for instance, a participant enters their food and/or supplement intake for a defined time period in the DHA intake application 27. That information is sent from the communication device 25 of the user device 14 to the host system 12 where the processor 35 registers the information in the appropriate fields of the database 32 associated with the participant. The food item, frequency, and intake amount could then be viewed in the food items region, frequency region, and intake amount of each item region respectively, of the food intake region 127, for instance, on the output device 30 of the host system 12 of the system 10.

The doctor information region 128 of the participant add/edit region 124 may include regions designed to accept input from a user. Exemplary regions include, but are not limited to, a doctor name region, and a log-in name region. The regions of the doctor information region 128 may be associated with appropriate fields in the database 32 of the system 10.

The regions of the doctor information region 128 may allow the system 10 to facilitate communication between a doctor and a participant, for instance, by associating a doctor with a participant (e.g., user) in the database 32. The participant may elect to have the system 10 automatically send at least one of a report and alert to the doctor and/or the user's user device 14 in response to certain events. These events may include, but are not limited to, completion of an DHA intake FFQ, a DHA dietary intake relative to a recommended intake (which is referred to herein as a "baseline"), a DHA dietary intake being below a predefined level, e.g., a baseline, relative to a recommended intake, a current DHA dietary intake being different from a past DHA dietary intake, sending a dietary recommendation responsive to the DHA dietary intake being below a predefined baseline or sending a dietary recommendation responsive to the DHA dietary intake being above a predefined baseline, and an updated DHA dietary intake relative to the recommended intake being below a predefined baseline. The recommended intake can be set by a government and/or private industry for a particular geographic region. For example, the "Recommended Daily Intake" (RDI) is a daily intake level of a nutrient that is considered to be sufficient to meet the requirements of 97-98% of healthy individuals in every demographic in the United States. The RDI was developed in the United States, but has since been used in other countries and regions. The RDI is based upon the Recommended Dietary Allowance (RDA) which may be updated from time to time and used within various locals to determine the recommended intake of DHA. When standards from the present form of the Recommended Dietary Allowances are used, the recommended intake of DHA may be between 100 mg and 200 mg.

The baseline can be set as the top level or less than the top level of the range of the recommended intake of DHA. In some embodiments, the baseline can be set less than a predetermined percentage of the top level of the range of the recommended intake of DHA. The predetermined percentage can be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% of the top level of the range of the recommended intake of DHA. When the recommended intake of DHA is between 100 mg and 200 mg, the baseline can be set at a level equal to or less than 200 mg, such as, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg. It should also be understood that the baseline could be multiple values within a range, such as multiple values starting at less than the top level of the range of the recommended intake of DHA, less than a bottom level of the range of the recommended intake of DHA, or less than any number within the range from the bottom level to the top level. In some embodiments, the baseline may be above the top level of the range of the recommended intake of DHA. For example, a recommendation for consuming less DHA could be automatically provided to a user in the event the user was consuming more than the recommended intake of DHA.

The baseline may be between 0 mg to 200 mg, between 50 mg to 200 mg, between 25 mg to 200 mg, between 10 mg to 100 mg, or include multiple values between and/or including any two numbers within the ranges specified above, such as between 75 mg and 150 mg. In this instance, an alert and/or recommendation may be sent to the participant's user device 14 and/or the participant's doctor when the daily intake is 75 mg, 150 mg or any value in between, such as 80 mg, 100 mg, or 125 mg.

In addition, the system 10 may allow a doctor, whose information is associated with a participant in the database 32, to communicate with the participant. For instance, in one embodiment, the doctor may enter a message in one of the external systems 17 and transmit the message via the network 16 to the host system 12 where the processor 35 accesses the database 32 to verify that the doctor is associated with the participant. Once the host system 12 determines the doctor is associated with the participant, the processor 35 of the host system 12 determines the predetermined communication method associated with the participant in the database 32 and causes the host system 12 output device 30 to transmit via the network 16 the message, for instance, to the user device 14 to be displayed on the output device 20.

It will be recognized by one skilled in the art, that the system 10 may allow communication and/or at least one of a report and an alert to be sent to any users of the system 10 whose information has been associated with one another in the database 32.

The assessment results region 129 of the participant add/edit region 124 may include regions designed to accept input from a user. Exemplary regions include, but are not limited to, a daily DHA intake amount region, an assessment address region, and a DHA intake compared to recommended level region. The regions of the assessment results region 129 may be associated with appropriate fields in the database 32 of the system 10.

The assessment date region 130 of the participant add/edit region 124 may include regions designed to accept input from a user. Exemplary regions include, but are not limited to, a date of last assessment region. The regions of the assessment date region 130 may be associated with appropriate fields in the database 32 of the system 10.

REFERENCES

Avni-Barron O, et al. Preconception planning to reduce the risk of perinatal depression and anxiety disorders. Expert Review of Obstetrics & Gynecology. 2010; 5(4): 421-35.

Bergmann R L, et al. Supplementation with 200 mg/day docosahexaenoic acid from mid-pregnancy through lactation improves the docosahexaenoic acid status of mothers with a habitually low fish intake and of their infants [J]. Annals of Nutrition and Metabolism, 2008, 52(2): 157-166.

Cheruku S R, et al. Higher maternal plasma docosahexaenoic acid during pregnancy is associated with more mature neonatal sleep-state patterning. Am J Clin Nutr. 2002 September; 76(3):608-13.

Dahl L, et al. A short food frequency questionnaire to assess intake of seafood and n-3 supplements: validation with biomarkers. Nutr J. 2011; 10:127.1-10.

Philibert A, et al. Fish intake and serum fatty acid profiles from freshwater fish. Am J Clin Nutr 2006; 84:1299-307.

Freeman M P, et al. An open trial of omega-3 fatty acids for depression in pregnancy. Acta Neuropsychiatr. 2006a; 18:21-24.

Freeman M P, et al. Randomized dose-ranging pilot trial of omega-3 fatty acids for postpartum depression. Acta Psychiatr Scand. 2006b January; 113(1):31-5.

Furuhjelm C, et al. Fish oil supplementation in pregnancy and lactation may decrease the risk of infant allergy[J]. Acta Paediatrica, 2009, 98(9): 1461-1467.

Gao J X, et al. Fatty acid composition of mature human milk in three regions of China. Journal of Hygiene Research. 2011; 40(6): 731-5.

Harris W S, et al. Stearidonic acid-enriched soybean oil increased the omega-3 index, an emerging cardiovascular risk marker. Lipids. 2008 September; 43(9):805-11.

Helland I B, et al. Maternal supplementation with very-long-chain n-3 fatty acids during pregnancy and lactation augments children's IQ at 4 years of age. Pediatrics. 2003 January; 111(1):e39-44.

Hibbeln J R, et al. Maternal seafood consumption in pregnancy and neurodevelopmental outcomes in childhood (ALSPAC study): an observational cohort study. Lancet. 2007 Feb. 17; 369(9561):578-85.

Hibbeln J R. Seafood consumption, the DHA content of mothers' milk and prevalence rates of postpartum depression: a cross-national, ecological analysis. J Affect Disord. 2002; 69(1-3):15-29.

Huang H L, et al. Docosahexaenoic acid in maternal and neonatal plasma phospholipids and milk lipids of Taiwanese women in Kinmen: fatty acid composition of maternal blood, neonatal blood and breast milk. Lipids in Health and Disease 2013, 12:27:1-8.

Judge M P, et al. A docosahexaenoic acid-functional food during pregnancy benefits infant visual acuity at four but not six months of age. Lipids. 2007; 42(2):117-22.

Krauss-Etschmann S, et al. Decreased cord blood IL-4, IL-13, and CCR4 and increased TGF-beta levels after fish oil supplementation of pregnant women. J Allergy Clin Immunol. 2008; 121(2):464-470.e6.

Kulkarni A, et al. Association of omega-3 fatty acids and homocysteine concentrations in pre-eclampsia. Clin Nutr. 2011; 30(1):60-4.

Lapillonne A, et al. Postnatal docosahexaenoic acid deficiency is an inevitable consequence of current recommendations and practice in preterm infants. Neonatology. 2010; 98(4):397-403.

Li H J, et al. Survey of pregnancy plasma DHA and related food factors. China Public Health. 2000; 16(1): 47-48.

Makrides M, et al. LC-PUFA requirements during pregnancy and lactation. Am J Clin Nutr. 2000, 71, 307S-311S.

Malcolm C A, et al. Scotopic electroretinogram in term infants born of mothers supplemented with docosahexaenoic acid during pregnancy. Invest Ophthalmol Vis Sci. 2003 August; 44(8):3685-91.

McNamara R K, Carlson S E. Role of omega-3 fatty acids in brain development and function: potential implications for the pathogenesis and prevention of psychopathology. Prostaglandins Leukot Essent Fatty Acids. 2006 October-November; 75(4-5):329-49.

Mendez M A, et al. Maternal fish and other seafood intakes during pregnancy and child neurodevelopment at age 4 years. Public Health Nutr. 2009 October; 12(10):1702-10.

Meng L P et al. Survey on the fatty acids intake in pregnant women indifferent aquatic product intake regions. Acta Nutrimenta Sinica. 2008; 30(3): 249-252.

Morse N L. Benefits of docosahexaenoic acid, folic acid, vitamin d and iodine on foetal and infant brain development and function following maternal supplementation during pregnancy and lactation. Nutrients. 2012; 4:799-840.

Neff L M, et al. Algal docosahexaenoic acid affects plasma lipoprotein particle size distribution in overweight and obese adults. J Nutr. 2011 February; 141(2):207-13.

Olsen S F and Secher N J. Low consumption of seafood in early pregnancy as a risk factor for preterm delivery: prospective cohort study. BMJ. 2002; 324:447.

Olsen S F, et al. Duration of pregnancy in relation to fish oil supplementation and habitual fish intake: a randomised clinical trial with fish oil. Eur J Clin Nutr. 2007 August; 61(8):976-85.

Plourde M, Cunnane S C. Extremely limited synthesis of long chain polyunsaturates in adults: implications for their dietary essentiality and use as supplements. Appl Physiol Nutr Metab. 2007 August; 32(4):619-34.

Su K P, et al. Omega-3 fatty acids for major depressive disorder during pregnancy: results from a randomized, double-blind, placebo-controlled trial. J Clin. Psychiatry. 2008 April; 69(4):644-51.

Swanson D, et al. Omega-3 fatty acids EPA and DHA: health benefits throughout life. Adv. Nutr. 2012 January; 3(1): 1-7.

Wakai K, et al. Intake frequency of fish and serum levels of long-chain n-3 fatty acids: a cross-sectional study within the Japan Collaborative Cohort Study. J Epidemiol. 2005 November; 15(6):211-8.

Wang X L, et al. Study on the relationship between maternal intake of docosahexaenoic acid and the mental development of infant. Maternal and Child Health Care Of China. 2008; 23:2682-4.

Yang Y X, et al. Chinese food components. Peking University Medical Press 2009 version 2:286-295.

Zhang J, et al. Maternal and neonatal plasma n-3 and n-6 fatty acids of pregnant women and neonates in three regions in China with contrasting dietary patterns. Asia Pac. J Clin. Nutr. 2009; 18(3):377-88.

From the above description, it is clear that the inventive concept(s) disclosed herein are well adapted to carry out the objects and to attain the advantages mentioned herein, as well as those inherent in the inventive concept(s) disclosed herein. While the embodiments of the inventive concept(s) disclosed herein have been described for purposes of this disclosure, it will be understood that numerous changes may be made and readily suggested to those skilled in the art which are accomplished within the scope and spirit of the inventive concept(s) disclosed herein.

What is claimed is:

1. A method comprising:
   establishing communication between (i) at least one host system having a processor and (ii) at least one user device having an input device, an output device and a communication device;
   automatically registering, by the at least one host system, individualized diet data received from the communication device of the at least one user device of a user, the individualized diet data having parameters indicative of type and quantity of at least one of foods and supplements consumed by a user during a defined time period;
   automatically analyzing the parameters of the individualized diet data with at least one predetermined rule set indicative of concentrations of docosahexaenoic acid (DHA) in select foods and supplements to determine a level of DHA dietary intake by the user relative to a selected recommended intake of a plurality of different recommended intakes stored in a database and respectively associated with a plurality of user categories, the plurality of user categories comprises categories of pregnant women based on trimester or month of pregnancy and further comprises categories of lactating or postpartum women based on month or quarter after childbirth;
   automatically generating, by the at least one host system, an alert and transmitting the alert via at least one predetermined communication method, without user intervention, responsive to the DHA dietary intake by the user relative to the selected recommended intake being below a predefined baseline, the alert being transmitted from the at least one host system to the at least one user device and at least one predetermined third party.

2. The method of claim 1, wherein the predefined baseline includes one or more values within a range bounded by and including 100 mg per day and 200 mg per day.

3. The method of claim 1, wherein determination of the level of DHA dietary intake by the user is based on a combination of multiple predetermined rule sets.

4. The method of claim 1, wherein at least one predetermined rule set associated with the select foods includes regionally sourced foods.

5. The method of claim 1, further comprising updating at least one of the parameters indicative of type and quantity of the at least one of foods and supplements consumed by the user; and, analyzing, without user intervention, the updated parameter indicative of type and quantity of the at least one of foods and supplements consumed by the user to determine an updated DHA dietary intake.

6. The method of claim 5, further comprising automatically generating an updated report containing the updated DHA dietary intake and the selected recommended intake.

7. The method of claim 5, further comprising automatically generating an updated alert, without user intervention, and transmitting the updated alert via the at least one predetermined communication method responsive to the updated DHA dietary intake relative to the selected recommended intake being below the predefined baseline.

8. The method of claim 7, wherein the predefined baseline includes one or more values within a range bounded by and including 100 mg per day and 200 mg per day.

9. The method of claim 7, further comprising generating and transmitting a dietary recommendation report, without user intervention, responsive to the DHA dietary intake or the updated DHA intake relative to the selected recommended intake being below the predefined baseline.

10. The method of claim 1, further comprising storing, by the at least one host system, information regarding the at least one predetermined third party; and associating, by the at least one host system, the stored information regarding the at least one predetermined third party with the user.

11. A system comprising:
    a host system having a processor; and
    at least one computer readable medium storing a set of instructions that when executed by the processor cause the processor to:
    obtain and record individualized diet data in a database, the individualized diet data having parameters indicative of at least one of foods and supplements consumed by a user during a defined time period;
    extract and analyzing the parameters in the database to determine a DHA dietary intake, without manual intervention, and in real-time as the individualized diet data is recorded into the database; and
    generating and transmitting from the host system via at least one predetermined communication method, without user intervention, an alert responsive to the DHA dietary intake relative to a selected recommended intake being below a predefined baseline, the alert being transmitted to the user and to a predetermined third party, the selected recommended intake is one of a plurality of different recommended intakes stored in a database and respectively associated with a plurality of user categories, the plurality of user categories comprises categories of pregnant women based on trimester or month of pregnancy and further comprises categories of lactating or postpartum women based on month or quarter after childbirth.

12. The system of claim 11, wherein the predefined baseline includes one or more values within a range bounded by and including 100 mg per day and 200 mg per day.

13. The system of claim 11, wherein the set of instructions cause the processor to generate and transmit a dietary recommendation via the at least one predetermined communication method, without user intervention, responsive to the DHA dietary intake relative to the selected recommended intake being below the predefined baseline.

14. The system of claim 11, wherein the host system is configured to store information regarding the at least one predetermined third party and associate the stored information regarding the at least one predetermined third party with the user.

* * * * *